(12) United States Patent
Eliasson et al.

(10) Patent No.: US 6,326,407 B1
(45) Date of Patent: Dec. 4, 2001

(54) HYDROCARBON SYNTHESIS

(75) Inventors: Baldur Eliasson, Birmenstorf (CH); Chang-Jun Liu, Tianjin (CN); Eric Killer, Wettingen (CH)

(73) Assignee: ABB Research Ltd., Zurich (CH)

( * ) Notice: Subject to any disclaimer, the term of this patent is extended or adjusted under 35 U.S.C. 154(b) by 0 days.

(21) Appl. No.: 09/632,798

(22) Filed: Aug. 4, 2000

(30) Foreign Application Priority Data

Aug. 5, 1999 (EP) .................................................. 99810699

(51) Int. Cl.$^7$ ............................. C07C 27/00; C07C 2/24; C07C 2/00; H05F 3/00
(52) U.S. Cl. .................... 518/700; 518/715; 204/164; 585/700; 585/514; 585/943
(58) Field of Search .................................... 518/700, 715; 204/165; 585/700, 514, 943

(56) References Cited

U.S. PATENT DOCUMENTS 3,703,460   11/1972   Shair et al. .
5,068,485   11/1991   Iton et al. .
6,159,432 * 12/2000   Mallinson et al. .............. 422/186.04

FOREIGN PATENT DOCUMENTS

0900591A1   3/1999   (EP) .

* cited by examiner

Primary Examiner—Johann Richter
Assistant Examiner—J. Parsa
(74) Attorney, Agent, or Firm—Blank Rome Comisky & McCauley LLP

(57) ABSTRACT

A method of transforming a normally gaseous composition consisting essentially of methane into a material comprising a major portion, at least, of hydrocarbons containing at least two carbon atoms; the method comprising the steps of feeding the composition into a reactor including a first electrode means, a second electrode means and at least one layer of a normally solid dielectric material positioned between the first and the second electrode means; submitting the composition within the reactor in the presence of a normally solid catalyst to a dielectric barrier discharge; and controlling the dielectric barrier discharge to convert the normally gaseous composition into the material comprising a major portion, at least, of the hydrocarbons containing at least two carbon atoms.

14 Claims, 1 Drawing Sheet

HYDROCARBON SYNTHESIS

BACKGROUND OF THE INVENTION

The present invention relates to a method of transforming a normally gaseous composition consisting essentially of methane into a material comprising a major portion, at least, of hydrocarbons containing at least two carbon atoms. Furthermore the present invention relates to an apparatus for transforming a normally gaseous composition consisting essentially of methane into a material comprising a major portion, at least, of hydrocarbons containing at least two carbon atoms. Moreover, the present invention relates to a method of transforming a normally gaseous mixture consisting essentially of normally gaseous hydrocarbons into a product stream, at least a portion of which containing normally liquid hydrocarbons, and to an apparatus for transforming a normally gaseous mixture consisting essentially of normally gaseous hydrocarbons into a product stream, at least a portion of which containing normally liquid hydrocarbons.

Within the past years there has been an increased interest from both the academic and industrial community to develop processes for transforming gaseous hydrocarbons, in particular for transforming natural gas and methane as its principal constituent into more valuable higher hydrocarbons. The driving force of new research in this field derives from the considerable reservoir of natural gas and the desire to utilize recent gas finds.

PRIOR ART

Since methane is the principal constituent of natural gas, as indicated above, the major research activity has focused on the transformation of methane. There are two general pathways to upgrade methane into higher hydrocarbons, first, by way of indirect conversion mainly requiring syngas production in a first step, and second, by way of direct conversion. A major difficulty, in particular for direct methane conversion, is the high strength of the C—H bonds in the methane molecule causing methane to be a very stable molecule and its reactions to have a high activation energy. There are many ways to activate methane such as photochemical and electrochemical activation, laser-induced activation, and radiolysis, as well as catalytic or even thermal activation. However as reported by J. M. Fox in Catal. Rev.-Sci. Eng., 35 (1993) 169–212 (report being incorporated herein for all purposes by way of reference) the right combination to directly convert methane into higher hydrocarbons has yet to be discovered. So far the direct methane transformations show poor economics, low conversions and low yields making them not suitable for practical applications.

Plasmas have been found to be a versatile tool for the development of new industrial processes and products. The properties of plasmas can be modified and a distinction is made between thermal plasma and nonthermal plasma differing markedly in both discharge characteristics and applications.

The energy distribution of the gas molecules, ions and electrons in thermal plasma indicates that the system is in thermal equilibrium and thus close to thermodynamic equilibrium. The temperature in the discharge region is uniformly very high for all particles. Moreover, there is a high energy flux in the plasma volume as well as at the electrodes if present. Thermal plasmas are therefore often called "hot plasmas". Hot plasmas include, in particular, arc discharges. An essential condition for the formation of a thermal plasma is a sufficiently high working pressure usually being over 10 kPa. The resulting large number of collisions between particles, in particular between electrons and heavy positive ions or neutral particles, leads to rapid redistribution of energy so that equilibrium is reached.

Nonthermal plasmas, in contrast, are far from thermodynamic equilibrium. Nonthermal plasmas have comparatively low gas temperatures and energy-conversion rates. Thus, the electrons in these plasmas have typically a very much higher temperature than the heavy ions and neutral particles. Nonthermal plasmas are therefore also named "cold plasmas". This group typically includes glow and silent discharges.

Cold plasma, particularly, silent gas discharges have demonstrated its suitability for large-scale industrial applications. The ozone generation, as its most important industrial application so far, is described by Eliasson et al. in IEEE Transactions on Plasma science, Vol. 19 (1991), page 309–323 and 1063–1077 (these reports being incorporated herein for all purposes by way of reference). It is to be noted that a characteristic of the silent discharge is the presence of a dielectric. Therefore silent gas discharges are also referred to as dielectric barrier discharges.

Plasma pyrolysis of methane has been operated for a long time to produce acetylene and carbon black with hydrogen as a by-product. Such plasma cracking usually requires a thermal plasma. As indicated, transformations via thermal plasma are typically high temperature processes and often requires an extra immmediate quenching step to get a sufficient selectivity of the desired products. This induces a complex system. A lot of energy is thereby consumed and wasted respectively due to the heating and cooling of the reaction gases that reduces the energy-efficiency and leads though to an significant increase of the production costs.

Recently, non-thermal plasmas have been found to be effective in the activation of methane at low temperature and atmospheric pressure. Thus, in a report by L. M. Zhou, B. Xue, U. Kogelschatz and B. Eliasson in Plasma Chemistry and Plasma Processing, Vol. 18 (1998), No. 3, 375–393 (this report being incorporated herein for all purposes by way of reference) and in DE 196 05 547 a method of producing methanol by subjecting a gaseous mixture containing methane and oxygen and/or nitrogen to a dielectric barrier discharge is disclosed. In the attempt to shift the selectivity towards the formation of higher hydrocarbons the inventors of the above-mentioned DE 196 05 547 conducted a series of experiments, in which pure methane was submitted to a dielectric barrier discharge (B. Eliasson, U. Kogelschatz, E. Killer and A. Bill in Proceedings of the 11th World Hydrogen Energy Conference, Stuttgart, Germany, Jun. 23–28, 1996, Vol. 3, 2449–2459; this report being incorporated herein for all purposes by way of reference). The major products were hydrogen and ethane with small amount of higher hydrocarbons. However, carbon black in fine particles was formed, in particular, on the surface of the dielectric material. The formation of carbon black is highly undesired since it changes the performance of the dielectric barrier discharge plasma and induces some uncertain phenomena for long term operation.

OBJECTS OF THE INVENTION

Accordingly, it is an object of the present invention to provide for a method of transforming a normally gaseous composition consisting essentially of methane into higher hydrocarbon products, particularly, into a material comprising a major portion, at least, of hydrocarbons containing at least two carbon atoms, which method can be carried out economically, at low pressures and low temperatures and preferably at ambient conditions.

It is another object of the present invention to provide for a method, which transforms a normally gaseous composition consisting essentially of methane in reasonable yields, and particularly, in a direct manner into higher hydrocarbon products.

It is a further object of the present invention to provide for a method of transforming a normally gaseous mixture consisting essentially of normally gaseous hydrocarbons into products at least a portion of which contain normally liquid hydrocarbons, which method can be carried out economically, at low pressures and low temperatures.

It is another object of the present invention to provide for a method that produces normally liquid hydrocarbons in reasonable yields from normally gaseous hydrocarbons. A further object of the present invention is a method for transforming normally gaseous hydrocarbons into normally liquid hydrocarbons, which liquid hydrocarbons are free of sulfur and heavy metal elements.

It is again a further object of the present invention to provide for a method of transforming a normally gaseous composition consisting essentially of methane into a material comprising a major portion, at least, of hydrocarbons containing at least two carbon atoms by way of a dielectric barrier discharge, which method substantially suppresses the formation of carbon black.

It is a further object of the present invention to provide for a method of transforming a normally gaseous mixture consisting essentially of normally gaseous hydrocarbons into products at least a portion of which contain normally liquid hydrocarbons, and which method substantially prevents the formation of carbon black.

Another object of the present invention is to provide for an apparatus that allows the transformation of a normally gaseous composition consisting essentially of methane and normally gaseous hydrocarbons respectively into higher hydrocarbons.

Further objects and advantages of the present invention will become apparent as this specification proceeds.

BRIEF SUMMARY OF THE INVENTION

We have found that the objects can be achieved according to a first general embodiment of the invention by a method as set forth in claim 1. Accordingly, the invention provides for a method of transforming a normally gaseous composition consisting essentially of methane into a material comprising a major portion, at least, of hydrocarbons containing at least two carbon atoms, which method comprises the steps of feeding the normally gaseous composition into a reactor that includes a first electrode means, a second electrode means and at least one layer of a normally solid dielectric material positioned between the first and the second electrode means, submitting the normally gaseous composition within the reactor in the presence of a normally solid catalyst to a dielectric barrier discharge and controlling the dielectric barrier discharge to convert the normally gaseous composition into the material comprising a major portion, at least, of the hydrocarbons containing at least two carbon atoms.

In a second general embodiment the invention provides for a method of transforming a normally gaseous mixture consisting essentially of normally gaseous hydrocarbons into a product stream, at least a portion of the product stream containing normally liquid hydrocarbons, which method comprises the steps of feeding the normally gaseous mixture into a reactor that includes a first electrode means, a second electrode means and at least one layer of a normally solid dielectric material positioned between the first and the second electrode means, submitting the normally gaseous mixture within the reactor in the presence of a normally solid catalyst to a dielectric barrier discharge and controlling the dielectric barrier discharge to convert the normally gaseous mixture into the product stream, at least a portion of the product stream containing the normally liquid hydrocarbons.

In a third general embodiment the invention provides for an apparatus for transforming a normally gaseous composition consisting essentially of methane into a material comprising a major portion, at least, of hydrocarbons containing at least two carbon atoms.

In a fourth general embodiment the invention provides for an apparatus for transforming a normally gaseous mixture consisting essentially of normally gaseous hydrocarbons into a product stream, at least a portion of the product stream containing normally liquid hydrocarbons.

DEFINITIONS, DETAILED DESCRIPTION OF PREFERRED EMBODIMENTS AND ELEMENTS OF THE INVENTION

The term "about" as used herein before any numeral implies a variation of typically±10%.

The term "normal" with regard to boiling points, boiling ranges, physical states of matter and the like indicates that the value is understood as being corrected for "normal conditions", i.e. a temperature of 25° C. and an atmospheric pressure of 1013 mbar.

The term "layer" is used herein to refer to any planar or curved stratum having a width dimension that is substantially larger than its thickness dimension; typically, the width:thickness ratio is at least 10:1 and generally well above that value.

In the context of the present invention the term "hydrocarbons" stands for products consisting of hydrogen and carbon atoms and consisting essentially of aliphatic hydrocarbons either saturated, such as alkanes, and/or unsaturated, such as alkenes and/or alkynes. Cycloaliphatic and/or aromatic hydrocarbons may, however, be present in minor amounts.

Examples of normally gaseous compositions consisting essentially of methane used for the present invention are, particularly, the natural gases. It is known that depending from the geographic origin the composition of the different natural gases vary. In particular, the nature and concentration of by-components present aside from methane as well as the concentration of methane itself in the different types of natural gas are different for the various geographic origins. Since the concentration of methane within those different types of natural gas, however, are generally higher than about 75%, the geographic origin of the natural gas and its specific composition are not critical and any natural gas can be used for the present invention. It is, moreover, in accordance with and within the scope of the present invention to use any waste and exhaust gases deriving from industrial processes and consisting essentially of methane. Generally, a "composition consisting essentially of methane" as used herein refers to a composition, in which the amount of methane is higher than about 75 Vol.-%.

According to a preferred embodiment of the present invention the normally gaseous composition consists of substantially pure methane. "Substantially pure" as used herein refers to a purity of at least about 95 Vol.-%, preferably of at least about 98 Vol.-% and more preferably of at least about 99 Vol.-%.

Hydrocarbons produced from natural gas and methane respectively in accordance with the present invention generally do not contain pollutants, like sulfur and/or heavy metal elements. This represents a major advantage compared to hydrocarbons produced from petroleum, in particular, if the hydrocarbons are used as fuel. Since the reservoir of natural gas is much larger compared to the one of petroleum the present invention is very valuable not only from an economic point of view but also taking ecological aspects into consideration.

In a further preferred embodiment of the present invention the normally gaseous composition is essentially free of gaseous oxygen. In this context, "essentially free" indicates that the amount of oxygen present in the normally gaseous composition is lower than about 0.5 Vol.-%, preferably lower than 0.1 Vol.-% and most preferably lower than 0.01 Vol.-%. It is noteworthy, however, that no precautions are necessary to explicitly exclude gaseous oxygen or air and, therefore, traces of oxygen or air can still be present without departing from the scope of the present invention. The absence of oxygen or oxygen-containing co-reactants in the feed, in the range indicated above, leads to an increase in selectivity towards the desired higher hydrocarbon products. Therefore, in order to further shift the selectivity towards the formation of higher hydrocarbons it is preferred to omit any oxygen or oxygen containing co-reactants in the feed in the range indicated above.

The preferred normally solid catalyst is a member selected from the group of zeolites, aluminophosphates, silicoaluminophosphates, metalloaluminophosphates and metal oxides containing OH groups. Typically, the solid catalyst is a zeolite selected from the group of zeolite X, zeolite Y, zeolite A, zeolite ZSM-5 and zeolite 13X.

In a further preferred embodiment of the invention, the normally solid catalyst comprises at least one substance selected from the group of metal ions and group IA, IIa, IB, IIb and VIII elements of the periodic table. The latter mentioned elements, i.e. alkali, earth alkali elements as well as the elements of the zinc and the copper group and the iron groups of the periodic table can be present either in ionic or atomic form. Those normally solid catalysts are synthesized by procedures generally known to the man skilled in the art, such as any type of ion exchange reactions in the case of zeolites. Examples of those solid catalysts are the zeolites NaY, NaX, NaA or Fe-ZSM-5.

Particularly, the use of zeolites as the normally solid catalyst inhibits the formation of carbon black, in particular, the precipitation of carbon black on the surface of the dielectric material, thus, allowing a long term operation of the dielectric-barrier discharge reactor. Moreover, the use of zeolites limits the growth of the hydrocarbon chain. Consequently, an increased yield of normally gaseous hydrocarbons and/or liquid hydrocarbons, particularly of normally liquid hydrocarbons having a normal boiling range of between about 50° C. and about 210° C. results. Furthermore, applying "shape-selective catalysts", such as zeolites, leads to an increased tendency to form branched hydrocarbons, in particularly, of normally liquid branched hydrocarbons representing a high-quality fuel. Additionally, the function of catalysts, in particular of the zeolites, include the chemisorption of the gaseous composition consisting essentially of methane and the gaseous mixture consisting essentially of gaseous hydrocarbons.

The term "shape-selective catalyst" is intended to refer to a catalyst that owns a special structure to limit the diffusion of the reacting molecules and the formed product molecules through its framework. Only molecules with diameters smaller than the openings or pores of the shape-selective catalyst can pass through the catalyst. Moreover, an additional constraint is imposed by the size and shape of the pores with respect to possible transition states of the reaction.

Furthermore, the use of zeolites as the normally solid catalyst offers the advantage of having high concentrations of OH groups on the zeolite surfaces, i.e. on the outer surfaces of the zeolite as well as within the zeolite cavities. In addition to the high concentration of OH groups on zeolite surfaces, an important characteristic of zeolites is the natural coulombic field formed within the zeolite framework. Within this context it should be noted that both the concentration of OH groups and the strength of the natural coulombic field are controllable and adjustable. Generally, these two features allow the zeolites to easily respond to an external electric field, i.e. the zeolite becomes electrically charged more easily. The control of the dielectric barrier discharge according to the invention allows though to control these charges and electrostatic fields and, therefore, to control zeolite activity and selectivity in the conversion of a gaseous composition into a normally liquid fuel.

In another preferred embodiment of the present invention the product stream containing both the normally liquid hydrocarbons and normally gaseous hydrocarbons is recovered from the reactor and at least the normally gaseous hydrocarbons in the product stream are recirculated into the reactor.

Further preferred embodiments of the present invention are defined in the dependent claims.

Typically, an operating pressure in the range of from about 0.01 bar to about 30 bar, preferably from about 0.1 bar to about 10 bar at an operating temperature up to about 400° C. is maintained in the reactor. Preferably, the layer of the normally solid dielectric material has a thickness of between about 0.1 mm to about 5 mm.

In a further preferred embodiment of the present invention, the first electrode means has a first effective electrode surface and the second electrode means has a second effective electrode surface, the at least one layer of the normally solid dielectric material covering at least a portion of the effective surface of at least one of the first and the second electrode means, the normally solid catalyst covering at least a portion of the layer of the normally solid dielectric. Typically, the first and the second electrode means each have an essentially tubular form, one of the first and the second electrode means forming an outer shell while the other of the first and the second electrode means forms an inner shell; the inner shell being distanced from the outer shell by an essentially tubular gap; the at least one layer of the normally solid dielectric material being arranged in an essentially tubular form and covering at least a portion of the inner and/or the outer shell; the normally solid catalyst being arranged in an essentially tubular form and covering at least a portion of the at least one layer of the normally solid dielectric. Preferably, the tubular form is essentially cylindrical.

In another preferred embodiment of the inventive apparatus, the first and the second electrode means each are provided by at least one essentially planar structure, the first electrode being distanced from the second electrode means by at least one essentially planar gap; the at least one layer of the normally solid dielectric being provided by at least one essentially planar structure and covering at least a portion of the first and/or the second electrode means; the normally solid catalyst being provided by at least one essentially planar form and covering at least a portion of the at least one layer of the normally solid dielectric material.

Typically, a plurality of pairs of first and second electrode means are arranged in an essentially parallel or stacked configuration forming a plurality of gaps, the gaps being connected in series to form an elongated path for passage of the normally gaseous composition consisting essentially of methane and the normally gaseous mixture consisting essentially of normally gaseous hydrocarbons respectively.

BRIEF DESCRIPTION OF THE DRAWINGS

For a better understanding of the nature and scope of the present invention—and not to limit the invention—preferred embodiments and details of the present invention are described in more detail in the following by reference to the drawings, in which.

DETAILED DESCRIPTION OF THE DRAWINGS

Figure 1:
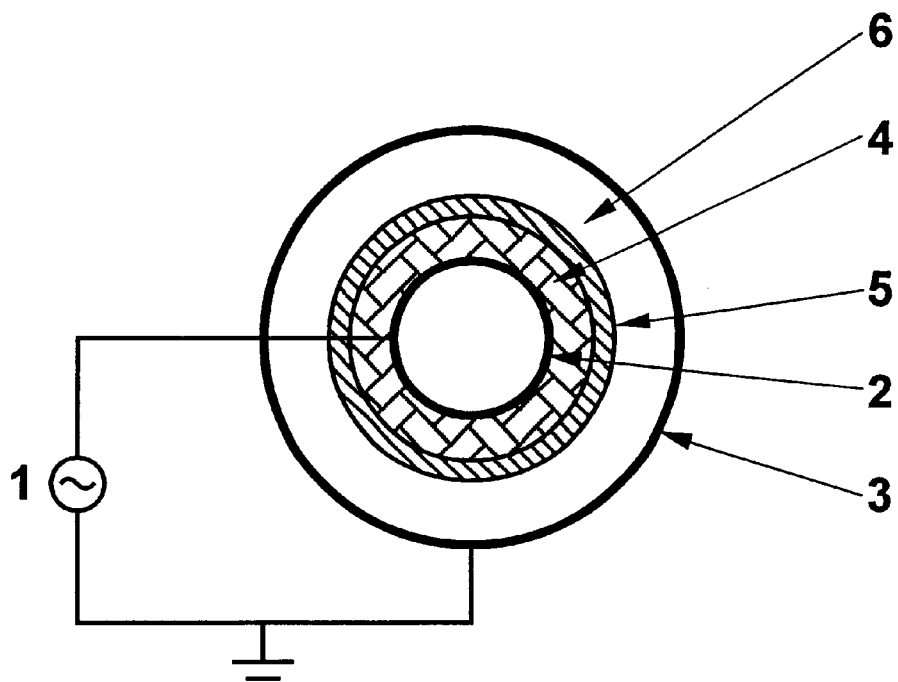
FIG. 1 is a diagrammatic cross sectional view of a preferred dielectric barrier discharge reactor configuration according to the invention.

The dielectric barrier discharge is a high pressure non-equilibrium discharge which occurs when alternating voltages are applied to a gas space between two electrodes separated by a non-conducting medium. FIG. 1 shows schematically a cross sectional view of a dielectric barrier discharge reactor according to the invention. The high voltage AC generator 1 is connected to the first electrode 2 and to the second grounded electrode 3 both having an essentially cylindrical form. The electrodes are generally made of corrosion-resistant metals or alloys or of materials covered by at least one layer of an electrically conducting substance. Electrode 2 forms an outer shell and electrode 3 forms an inner shell. The dielectric layer 4 is typically a glass, quartz or ceramic tube having a thickness of between about 0.1 mm and about 5 mm and covers the effective surface of electrode 2. The shape-selective catalyst 5 shown in FIG. 1, is also formed in essentially cylindrical form and is provided to cover the dielectric layer 4. Typically, the dielectric tube 4 serves as support for the solid catalyst 5. So, the solid catalyst 5, typically in powder form, is disposed in a piece of gas-permeable quartz fleece and wrapped around the outer surface of the dielectric tube 4, i.e. the surface of the dielectric tube 4 facing towards the electrode 3. Further catalyst support arrangements preferably used for the present dielectric barrier discharge reaction are described in the DE-197'35'785 (the disclosure of which being incorporated herein for all purposes by way of reference). It is obvious that the form and the size of the solid catalyst, i.e. whether it is applied in powder form or as grains of different sizes and the manner by which the catalyst is supported, i.e by means of the dielectric material and by means of an additional support respectively, can be modified within the scope of the present invention.

The normally gaseous composition consisting essentially of methane and the normally gaseous mixture consisting essentially of normally gaseous hydrocarbons respectively passes through the essentially cylindrical discharge gap 6, where it is exposed to the dielectric barrier discharge. The dielectric barrier discharge is effected by an AC potential applied between the first electrode and the second electrode means. The preferred AC potential being in the range of from about 6 kV to about 100 kV and the frequency of the AC potential preferably being in the range of from about 50 Hz to about 1 MHz. As indicated above, an operating pressure in the range of from about 0.01 bar to about 30 bar, preferably from about 0.1 bar to about 10 bar, at an operating temperature up to about 400° C. is maintained in the reactor. The normally gaseous composition consisting essentially of methane and the normally gaseous mixture consisting essentially of normally gaseous hydrocarbons respectively is passed through the reactor preferably at a rate of from about 0.1 m$^3$/hour to about 200 m$^3$/-hour.

When the amplitude of applied AC electric field reaches a critical value, breakdown is initiated in the gas and a current flows from one electrode to the other. Once breakdown is initiated at any location within the discharge gap, charge accumulates on the dielectric and leads to the formation of an opposite electric field. This opposite electric field reduces the external electric field within the gap and interrupts the current flow in a few nanoseconds to form microdischarges. The duration of the current pulse relates to pressure and properties of gases involved and the dielectrics applied. A large number of such microdischarges will be generated when a sufficiently high AC voltage is applied. The principal advantages of dielectric barrier discharge are: it combines the large volume excitation of glow discharges with high pressure characteristics of corona discharges; the entire electrode area is effective for discharge reactions.

Figure 2:
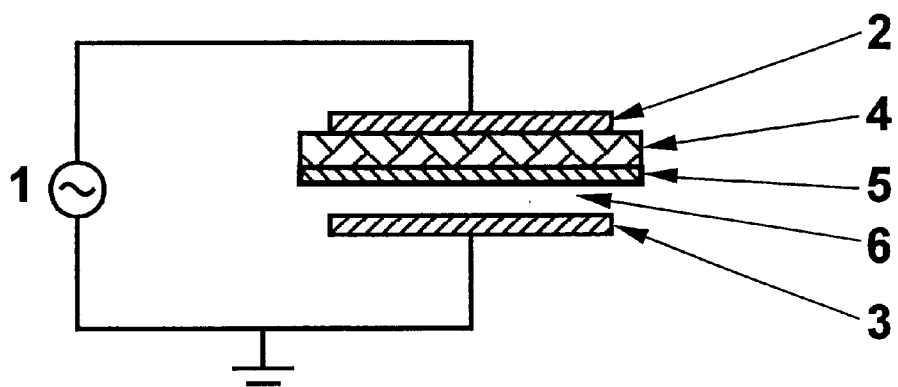
FIG. 2 is a diagrammatic cross sectional view of a further preferred dielectric barrier discharge reactor configuration according to the invention.

FIG. 2 shows another preferred configuration of a dielectric barrier discharge reactor according to the invention. The corresponding electrodes, the layer of the normally solid dielectric material and the normally solid catalyst respectively of this embodiment have or are arranged in an essentially planar form. Examples of the dielectric material are glass, as indicated, as well as quartz, ceramics, $ZrO_2$ or $Al_2O_3$.

Further preferred dielectric barrier discharge reactor configurations not being shown in the FIGS. 1 and 2 are those, where the solid catalyst either occupies an essential part of the discharge gap 6 or where the solid catalyst covers only a portion of the dielectric material.

EXAMPLES

Example 1

The feed gas, i.e. methane, was introduced into the system flowing downstream through the reactor. The operative conditions were as follows: a flow rate of 150 ml/min, a temperature of 150° C., a pressure of 1 bar and 500 w applied power. A dielectric barrier discharge is thus initiated. The catalyst used is NaX zeolite. A back pressure valve at the exit of the reactor was used to adjust the pressure. A MTI (Microsensor Technology Inc., M200H) dual-module micro gas chromatograph containing a Poraplot Q column and a molecular sieve 5A Plot column with a TCD detector was used to detect gaseous products. The gas sample was heated by heated lines to avoid possible condensation before it was taken into the GC. The liquid sample was also gas-chromatographically analyzed.

The partial pressures and selectivites of products formed in Example 1 are reported in Table 1. The conversion of methane was 26.8% according to the following equation:

$$\text{Conversion } [CH_4] = \{([CH_4]_{in} - [CH_4]_{out})/[CH_4]_{in}\} \times 100\%$$

The selectivity of the products are defined as:

$$\text{Selectivity [prod.]} = \{(\text{number of carbon atoms of prod.} \times [\text{prod.}]_{out})/ \text{total carbon amount converted}\} \times 100\%$$

TABLE 1

Partial pressures and selectivities of products in gas phase

| Product | Partial pressure in the gas phase (mbar) | Selectivity (%) |
|---|---|---|
| $C_2H_4$ | 8.910 | 6.854 |
| $C_2H_6$ | 28.468 | 21.900 |
| $C_2H_2$ | 10.86 | 8.355 |
| $C_3H_6$ | 4.898 | 5.652 |
| $C_3H_8$ | 18.635 | 21.503 |
| $C_4H_8$ | 0.362 | 0.556 |
| $C_4H_{10}$ | 3.961 | 6.095 |
| $i$-$C_4H_{10}$ | 4.136 | 6.363 |
| $C_5H_{10}$ | 0.204 | 0.393 |
| $C_5H_{12}$ | 0.552 | 1.062 |
| 2-methylbutane | 2.606 | 5.012 |
| 2,2-dimethylpropane | 0.568 | 1.092 |
| $C_6H_{14}$ | 0.193 | 0.446 |
| others | | 14.717 |

As listed in Table 1 the total selectivity for higher hydrocarbons is 100%. Most of the products are normally gaseous hydrocarbons, i.e hydrocarbons containing up to 4 carbon atoms. In particular, hydrocarbons containing two or three carbon atoms are formed. Note that products summarized as 'others' in Table 1 are substantially hydrocarbons containing 6 to 11 carbon atoms. Thus, the total yield for gasoline components, i.e hydrocarbons containing 5 to 11 carbon atoms, is 21.3%, from which a large amount are branched hydrocarbons. The latter is of importance since branched hydrocarbons represent a better fuel because of the phenomenon of engine knock.

Although certain preferred embodiments and examples of the invention have been described herein, it will be apparent to those skilled in the art to which the invention pertains that modifications and variations of the described embodiments may be made without departing from the spirit and scope of the invention.

LIST OF REFERENCE SIGNS

1 high voltage ac generator
2 first electrode means
3 second electrode means
4 dielectric layer, dielectric material
5 discharge gap
6 catalyst

What is claimed is:

1. A method of transforming a normally gaseous composition consisting essentially of methane into a material comprising a major portion, at least, of hydrocarbons containing at least two carbon atoms; said method comprising the steps of:

feeding said normally gaseous composition into a reaction including a first electrode means, a second electrode means and at least one layer of a normally solid dielectric material positioned between said first and said second electrode means;

submitting said normally gaseous composition within said reactor in the presence of a normally solid catalyst to a dielectric barrier discharge, and controlling said dielectric barrier discharge to convert said normally gaseous composition into said material comprising a major portion, at least, of said hydrocarbons containing at least two carbon atoms; wherein said normally gaseous composition consists of substantially pure methane having a purity of at least about 95 Vol. % and is essentially free of gaseous oxygen in that the oxygen content of said normally gaseous composition is lower than about 0.5 Vol. %.

2. The method of claim 1 wherein said normally gaseous composition consists of substantially pure methane having a purity of at lest about 98 Vol. % and is essentially free of gaseous oxygen in that the oxygen content of said normally gaseous composition is lower than about 0.1 Vol. %.

3. The method of claim 1 wherein said normally gaseous composition consists of substantially pure methane having a purity of at least about 99 Vol. % and is essentially free of gaseous oxygen in that the oxygen content of said normally gaseous composition is lower than about 0.01 Vol. %.

4. The method of claim 1 wherein said normally solid catalyst is selected from the group consisting of zeolites, aluminophosphates, silicoaluminosphosphates and metalloaluminophosphates.

5. The method of claim 4 wherein said zeolite is a member selected from the group of zeolite X, zeolite Y, zeolite A, zeolite ZSM-5 and zeolite 13X.

6. The method of claim 4 wherein said normally solid catalyst is a NaX zeolite.

7. The method of claim 1, further including the step of applying an AC potential between said first and second electrodes.

8. The method of claim 7, further including the step of applying an AC potential between said first and second electrodes.

9. The method of claim 7, wherein said applied AC potential is in the range of from about 6 kV to about 100 kV and the frequency of the AC potential is in the range of from about 50 Hz to about 1 Mhz.

10. The method of claim 8, wherein said applied AC potential is in the range of from about 6 kV to about 100 kV and the frequency of the AC potential is in the range of from about 50 Hz to about 1 Mhz.

11. The method of claim 7, further including the step of maintaining the operating pressure of said normally gaseous mixture in the range of from about 0.01 bar to about 30 bar at an operating temperature up to about 400° C.

12. The method of claim 8, further including the step of maintaining the operating pressure of said normally gaseous mixture in the range of from about 0.01 bar to about 30 bar at an operating temperature up to about 400° C.

13. The method of claim 1, further including the step of recovering a product stream, at least a portion of which comprises normally liquid hydrocarbons.

14. The method of claim 7, further including the step of recovering a product stream, at least a portion of which comprises normally liquid hydrocarbons.

\* \* \* \* \*